United States Patent
Fukuoka et al.

(10) Patent No.: US 9,920,064 B2
(45) Date of Patent: Mar. 20, 2018

(54) SOLID CATALYST FOR DEHYDRATION OF SUGAR ALCOHOL AND METHOD FOR PREPARING DIANHYDROSUGAR ALCOHOL USING SAID CATALYST

(71) Applicants: National University Corporation Hokkaido University, Hokkaido (JP); Clariant Catalysts (Japan) K.K., Tokyo (JP)

(72) Inventors: Atsushi Fukuoka, Hokkaido (JP); Hirokazu Kobayashi, Hokkaido (JP); Bo Feng, Hokkaido (JP); Haruka Yokoyama, Hokkaido (JP); Xin Chen, Toyama (JP)

(73) Assignees: CLARIANT CATALYSTS (JAPAN) K.K., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 0 days.

(21) Appl. No.: 15/322,584

(22) PCT Filed: Jul. 3, 2015

(86) PCT No.: PCT/JP2015/003365
§ 371 (c)(1),
(2) Date: Dec. 28, 2016

(87) PCT Pub. No.: WO2016/009607
PCT Pub. Date: Jan. 21, 2016

(65) Prior Publication Data
US 2017/0166579 A1 Jun. 15, 2017

(30) Foreign Application Priority Data
Jul. 16, 2014 (JP) .................................. 2014-146149

(51) Int. Cl.
C07D 493/00 (2006.01)
C07D 493/04 (2006.01)
B01J 29/70 (2006.01)

(52) U.S. Cl.
CPC ........ *C07D 493/04* (2013.01); *B01J 29/7007* (2013.01)

(58) Field of Classification Search
CPC .......................... C07D 493/04; B01J 29/7007
(Continued)

(56) References Cited

U.S. PATENT DOCUMENTS 6,689,892 B2  2/2004  Andrews et al.
6,864,378 B2  3/2005  Bhatia
(Continued)

FOREIGN PATENT DOCUMENTS

CA  2340348 A1  3/2000
JP  H08-206507 A  8/1996
(Continued)

OTHER PUBLICATIONS

Hoefnagel et al, Selective alkylation of methylbenzenes with cyclohexene catalyzed by solid acids, Catalysis Letters vol. 85, Nos. 1-2, Jan. 2003, p. 7-11.*
(Continued)

*Primary Examiner* — Taylor V Oh
(74) *Attorney, Agent, or Firm* — Scott R. Cox

(57) ABSTRACT

The present invention addresses the problem of providing a solid catalyst capable of achieving high selectivity and high yield for isosorbide, preferably at the same time, in a dehydration reaction by which dianhydrosugar alcohol is obtained from a sugar alcohol, particularly, in a dehydration reaction by which isosorbide is obtained from sorbitol.
The above-mentioned problem is solved by a solid catalyst for a dehydration reaction for preparing dianhydrosugar
(Continued)

alcohol from sugar alcohol, said catalyst including an H-type β zeolite having an atomic composition ratio of Si to Al (Si/Al) of more than 20.

9 Claims, 2 Drawing Sheets

(58) Field of Classification Search
USPC .......................................................... 549/464
See application file for complete search history.

(56) References Cited

U.S. PATENT DOCUMENTS

| | | |
|---|---|---|
| 9,120,806 B2 | 9/2015 | Schreck et al. |
| 2002/0028959 A1* | 3/2002 | Andrews .............. C07D 493/04 549/465 |

FOREIGN PATENT DOCUMENTS

| | | |
|---|---|---|
| JP | 11-199576 A | 7/1999 |
| WO | WO2007103586 A2 | 9/2007 |

OTHER PUBLICATIONS

Freese et al, Acylation of aromatic compounds on H-Beta zeolites, Catalysis Today 49, 1999, p. 237-244.*
Chen et al, Comparison of canola oil conversion over MFI, BEA, and FAU, Applied Catalysis A; General 384, 2010, p. 206-212.*
International Search Report dated Oct. 6, 2015 with respect to international application No. PCT/JP2015/003365.
Honglin, Wang et al: "Surface Acidity of H-beta and its catalytic activity for alkylation of benzene with propylene", Catalysis Letters, Springer New York LLC, United States, vol. 76, No. 3-4, Oct. 1, 2001, pp. 225-229.
Extended European Search Report dated Nov. 8, 2017 with respect to European Patent Application No. 15822269.5 (PCT/JP2015/003365).

* cited by examiner

[Fig. 1]
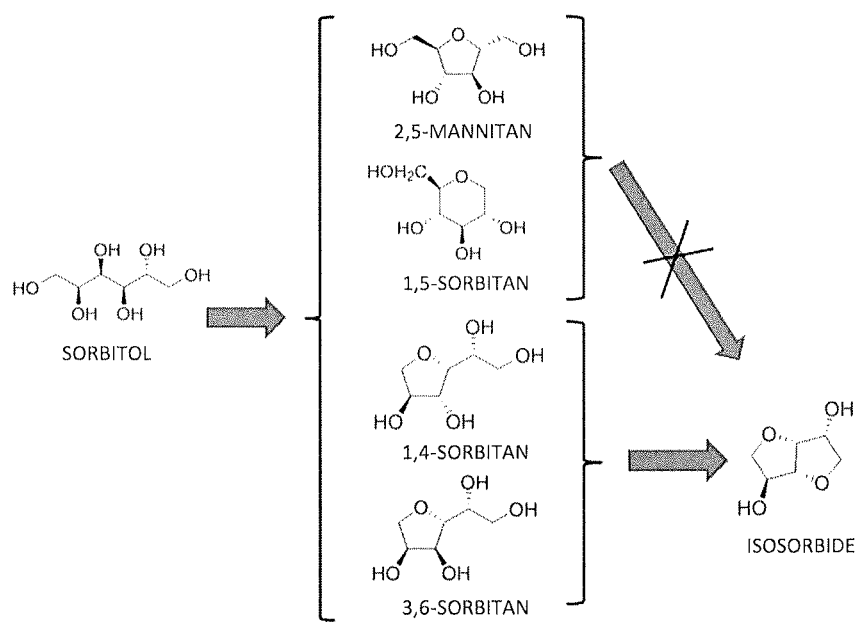

[Fig. 2]
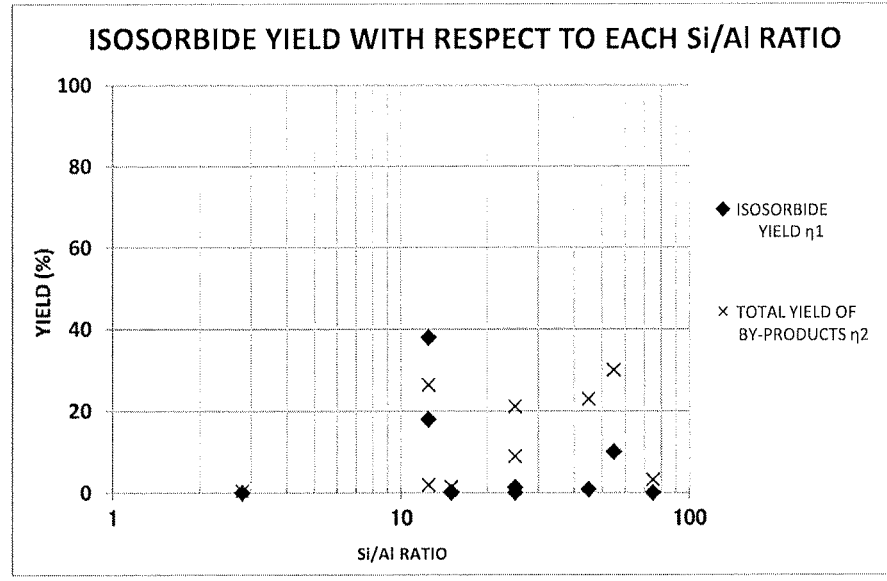
PLOT OF ISOSORBIDE YIELD η1 AND TOTAL YIELD OF BY-PRODUCTS η2 WITH RESPECT TO Si/Al RATIO FOR ZEOLITES DISCLOSED IN EXAMPLES AND COMPARATIVE EXAMPLES IN PATENT LITERATURE 1
[Fig. 3]
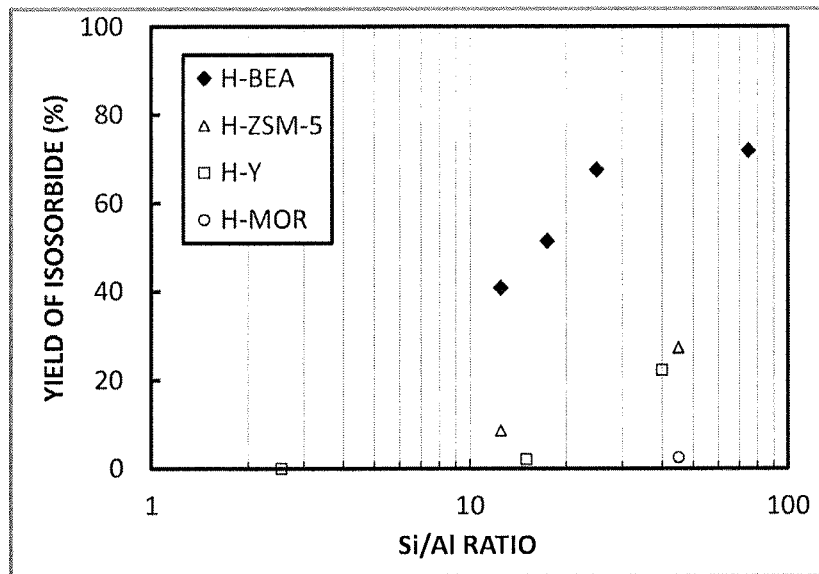
RELATIONSHIP BETWEEN ISOSORBIDE YIELD AND THE TYPES OF ZEOLITE AND Si/Al RATIO (H-BEA: ACID-TYPE β ZEOLITE)

SOLID CATALYST FOR DEHYDRATION OF SUGAR ALCOHOL AND METHOD FOR PREPARING DIANHYDROSUGAR ALCOHOL USING SAID CATALYST

TECHNICAL FIELD

The present invention relates to a catalyst for removing two water molecules from a sugar alcohol derived from cellulose to produce a dianhydrosugar alcohol, and a method for producing a dianhydrosugar alcohol using the catalyst, and preferably relates to a catalyst for producing isosorbide from sorbitol, and an improved method for synthesizing isosorbide using the same.

BACKGROUND ART

In recent years, the development of chemical reaction processes utilizing forest resources and biomass instead of petroleum resources has thrived and sugar alcohols derived from cellulose and the development of their applied uses have attracted attention. One example of this is a process for dehydrating a sugar alcohol to obtain the raw material of a useful chemical substance. For example, an isosorbide that is a dianhydrosugar alcohol obtained by dehydrating sorbitol obtained by cellulose decomposition is useful for the production of raw materials used in medicinal compounds and the production of condensation polymers such as polyurethanes, polycarbonates and polyesters, and therefore catalysts for improving its reaction yields have been actively developed as shown, for example, in Patent Literature 1.

The reaction for obtaining isosorbide from sorbitol comprises a two-stage dehydration reaction as shown by the chemical reaction formula in FIG. 1. Sorbitol has six hydroxyl groups in the molecule, and therefore many types of intermediates are produced by the dehydration reaction of sorbitol, and particular ones among them can produce isosorbide. There are many types of side reactions in this manner, and therefore there are great difficulties involved in the development of a catalyst for increasing the yield of isosorbide, and a chemical reaction control technique using said catalyst.

For example, in Patent Literature 1, regarding the reaction for obtaining isosorbide from sorbitol, many experiments are performed using, as catalyst for the dehydration of sorbitol, a sulfuric acid that is a homogeneous acid catalyst or zeolites as heterogeneous catalysts. Among said experiments, for various zeolites, a maximum yield of only about 38% is obtained in a reaction time as long as 12 hours (Example 13), whereas for sulfuric acid, a yield of more than 70% is obtained in a reaction time of 75 minutes (Example 3). In this manner, sulfuric acid gives a very high yield compared with zeolite catalysts in a shorter amount of time, and therefore it has been widely used as a catalyst for isosorbide production.

Despite the high yield and low cost, using a sulfuric acid catalyst in this manner poses many industrial problems. In particular, there are a number of factors that can increase costs. For example, because it is a homogeneous catalyst, it is necessary to separate and purify the isosorbide after completion of the reaction, and the cost of the equipment and steps needed for said separation and purification is considerable. In addition, the aforementioned separation and purification further entail the complicated issue of the neutralization and disposal of the separated and remaining waste sulfate. Furthermore, appropriate steps must be taken to prevent the corrosion of the chemical reaction apparatus by sulfuric acid.

Therefore, the development of techniques for minimising the drawbacks of sulfuric acid has also been promoted, and as an example thereof, an attempt to use various solid (heterogeneous) catalysts is shown in the above Patent Literature 1. In Patent Literature 1, for various zeolites such as H-β zeolites (acid type β zeolites), H-mordenites and H-ZSM-5, as solid acid catalysts, the isosorbide production yield is measured while modifying conditions such as the Si/Al ratio, reaction time and the amount of the acid catalyst added. The excerpted and summarized results are shown in the following Table 1. Among these solid catalysts, the use of the H-type β zeolite with Si/Al=12.5 produces the highest yield (38%) in a reaction time of 12.3 hours. The zeolite-based catalysts in Table 1 need a very long reaction time and have very low yield, compared with the sulfuric acid catalysts used which yield more than 70% in a reaction time of 75 minutes, and therefore the zeolite-based catalysts have poor practicality. In Patent Literature 1, for sulfated zirconia, a high yield of 73% is obtained (Example 23), but the durability is low, and therefore sulfated zirconia is not practical for mass synthesis uses.

TABLE 1

Excerpts of Data in Examples and Comparative Examples in Patent Literature 1

| Example | Name | Si/Al | Isosorbide yield | Total yield of by-products | Reaction time (hours) | Amount of catalyst added (% by weight) | Reaction temperature (° C.) |
|---|---|---|---|---|---|---|---|
| Example 11 | H-β | 12.5 | 18.0 | 26.4 | 5.0 | 9.3 | 150.0 |
| Example 12 | DAY-55 | 55.0 | 10.0 | 30.0 | 5.1 | 9.4 | 150.0 |
| Example 15 | H-Y | 25.0 | 1.3 | 21.1 | 5.1 | 9.4 | 150.0 |
| Comparative Example 18 | USY | 2.8 | 0.0 | 0.4 | 5.0 | 9.3 | 150.0 |
| Example 17 | H-ZSM-5 | 15.0 | 0.2 | 1.5 | 5.0 | 9.4 | 150.0 |
| Comparative Example 20 | H-ZSM-5 | 25.0 | 0.0 | 8.9 | 5.0 | 9.3 | 150.0 |
| Comparative Example 21 | H-ZSM-5 | 75.0 | 0.0 | 3.2 | 5.0 | 9.5 | 150.0 |
| Example 16 | H-mordenite | 45.0 | 0.8 | 22.9 | 5.1 | 9.3 | 150.0 |
| Comparative Example 22 | H-mordenite | 15.0 | 0.0 | 1.4 | 5.0 | 9.3 | 150.0 |
| Example 13 | H-β | 12.5 | 38.0 | 1.9 | 12.3 | 20.0 | 150.0 |

Considering that the dominant factor of the dehydration reaction from sorbitol to isosorbide is the high acidity resulting from the sulfuric acid catalyst, it is expected that, the yield of isosorbide will also increase for these various zeolites, when those having a high acidity are used as catalysts. Their acidity depends on both the concentration of active sites and the intensity of each activity. It is considered that the acidity of a zeolite as a Bronsted acid depends on the entry of Al into the Si network, and it is said that there is a large acid content in a region in which the Al composition is relatively large, i.e. a region in which the Si/Al atomic ratio is small. For example, in Patent Literature 2, zeolites are studied as solid acid catalysts for the dehydration reaction of an alcohol, and in its specification, it is disclosed that the acidity is highest in the range of Si/Al=5 to 20 (paragraph [0009], Patent Literature 2).

From the above point of view, for the data in the Examples and the Comparative Examples in Patent Literature 1 (Table 1), the isosorbide yield $\eta_1$ and the total yield of by-products $\eta_2$ with respect to the Si/Al ratio are plotted as shown in FIG. 2. Here, no fixed relationship is noted between the yield of isosorbide $\eta_1$ and the Si/Al ratio, and a tendency for one with a high isosorbide yield $\eta_1$, to also have a high yield of by-products $\eta_2$ is noted.

In addition, for the H-type β zeolites, a relatively high yield (38%) is obtained at Si/Al=12.5 as described above, but an impractically long reaction time of 12 hours is required, about 10 times longer than that required for the sulfuric acid catalyst. From the above data based on Patent Literature 1, it seems that it is difficult to obtain, with a solid catalyst having low price and good durability, a yield of about 70% at 150° C. or less in a reaction time of about 1 to 3 hours as with the sulfuric acid catalyst.

With respect to the durability of the solid catalyst described above, both durability for high temperature, chemical action and the like during the reaction, and durability for regeneration treatment performed when the activity decreases are important. In a dehydration reaction with a solid acid catalyst, generally, with the progress of the reaction, the reaction active sites are covered due to carbon adhesion (caulking), causing a decrease in yield. In order to reduce activity deterioration due to caulking, it is important to decrease the dehydration reaction temperature as much as possible. But, when caulking occurs nevertheless, recycling in which the catalyst is subjected to washing and carbon removal is performed to extend the life of the catalyst. Therefore, it is very important in promoting practical use that the deterioration of the solid catalyst is minimised in the recycling step, and the repeated regeneration is stable.

As described above, the need to replace the conventional sulfuric acid catalyst by a solid acid catalyst having excellent handleability is high, but the fact is that a catalyst satisfying performance requirements such as a high reaction yield, recyclability and cost cannot be implemented yet.

CITATION LIST

Patent Literature

Patent Literature 1: Japanese Patent Publication No. 2004-501117-A
Patent Literature 2: Japanese Patent Publication No. H08-206507-A

SUMMARY OF INVENTION

Technical Problem

It is an object of the present invention to provide a solid catalyst that can, preferably simultaneously, achieve a high isosorbide selectivity and a high isosorbide yield in a dehydration reaction for obtaining a dianhydrosugar alcohol from a sugar alcohol, particularly in a dehydration reaction for obtaining isosorbide from sorbitol.

It is another object of the present invention to provide a solid catalyst that can achieve a yield almost equal to that of a conventional sulfuric acid catalyst (generally an $\eta_1$ of 65% or more in a reaction time of 2 hours) in a dehydration reaction for obtaining a dianhydrosugar alcohol from a sugar alcohol, particularly in a dehydration reaction for obtaining isosorbide from sorbitol.

It is another object of the present invention to provide a solid catalyst that allows for the synthesis of a dianhydrosugar alcohol from a sugar alcohol, particularly the synthesis of isosorbide from sorbitol, at a temperature lower than the conventional temperature, and provide an improved method for synthesizing isosorbide using said catalyst.

Further, it is another object of the present invention to provide a solid catalyst for producing a dianhydrosugar alcohol from a sugar alcohol, particularly producing isosorbide from sorbitol, which has excellent repeated regeneration performance (also referred to as "recyclability").

Other objects of the invention of this application will be apparent from the following description.

Solution to Problem

In view of the above actual circumstances, the inventors have studied diligently in order to solve the drawbacks of the conventional art, and as a result, have obtained the following guidelines as ideas for solving the problems of the present invention.

(1) Referring to the data in Example 1 in Patent Literature 1, in order to attain, with the zeolite catalysts, performance at the same level as with the sulfuric acid catalyst, it is necessary to shorten the reaction time to about one tenth and further nearly double the yield.
(2) In order to shorten the reaction time and increase the yield in such a manner, the selection of a catalyst having a high acidity and high selectivity and the design of the amount of the catalyst are necessary so that isosorbide can be attained even in the complicated reaction step.
(3) Following this guideline, it was expected that, for the dehydration reaction of sorbitol, a high yield would be obtained if the Si/Al ratio of a zeolite catalyst is small, since it is described in Patent Literature 2 that the acidity of a zeolite catalyst increases as the Si/Al ratio becomes smaller.
(4) However, from the data in Patent Literature 1, it is noted that a high yield cannot always be obtained by decreasing the Si/Al ratio.
(5) In addition, a trade-off tendency that, when an attempt is made to increase the yield of isosorbide m, the yield of by-products $\eta_2$ also increases is observed.
(6) From the result of the above (5), it has been presumed that even if the Si/Al ratio of the zeolite is decreased to increase acidity for easy dehydration, the selectivity decreases because of a steric effect and other reasons when the Si/Al ratio is decreased, and as a result the result of the above (5) is caused.
(7) Therefore, various acid catalysts have been screened again, and as a result it has been confirmed that when H-type β zeolites as well as particular ion exchange resins and the like are used, a relatively high m can be obtained.
(8) Ion exchange resins have low durability at a high temperature of 100° C. or more. Accordingly, for H-type β zeolites, by changing the Si/Al ratio thereof and further also considering reaction conditions such as the amount of the catalyst added and reaction temperature in combination, an optimal catalyst composition has been searched for.

(9) Surprisingly, as a result, it has been discovered that when an H-type β zeolite with more than Si/Al=20, not specifically shown in Patent Literature 1, is used as a catalyst, $\eta_1$ increases sharply with no increase in the yield of by-products $\eta_2$.

(10) Furthermore, it has been found that when the catalyst in the above (9) is used, a high reaction temperature is not always advantageous, and there is a preferred reaction temperature area.

(11) From the above findings, in the present invention, a high isosorbide yield equal to that obtained with a sulfuric acid catalyst has been found to be obtainable at a relatively low reaction temperature and in a short reaction time.

(12) Furthermore, a recycling test of the catalyst obtained in this manner was carried out, and a high yield $\eta_1$ of 60% or more, close to that obtained with a sulfuric acid catalyst, was achieved even after four repeated uses, arriving at the present invention.

Specifically, the present invention relates to the following:

1. A solid catalyst for a dehydration reaction for producing a dianhydrosugar alcohol from a sugar alcohol, comprising an H-type β zeolite having an atomic composition ratio of Si to Al (Si/Al) of more than 20.
2. The solid catalyst according to the above 1, wherein the Si/Al is 400 or less.
3. The solid catalyst according to the above 1, wherein the sugar alcohol is selected from a group consisting of sorbitol, mannitol and iditol.
4. The solid catalyst according to the above 3, wherein the sugar alcohol is sorbitol, and the dianhydrosugar alcohol is isosorbide.
5. A method for producing a dianhydrosugar alcohol from a sugar alcohol, comprising bringing the sugar alcohol into contact with the catalyst according to the above 1.
6. The method according to the above 5, wherein the amount of the H-type β zeolite contained in the catalyst is 5 to 60 parts by mass, based on 100 parts by mass of the sugar alcohol.
7. The method according to the above 5, comprising maintaining the sugar alcohol brought into contact with the catalyst under ambient pressure or under reduced pressure.
8. The method according to the above 5, comprising maintaining the sugar alcohol brought into contact with the catalyst at a temperature of 110° C. to 170° C.
9. The method according to the above 5, comprising maintaining the sugar alcohol brought into contact with the catalyst for 1.5 hours or more.
10. Use of an H-type β zeolite having an atomic composition ratio of Si to Al (Si/Al) of more than 20, as a solid catalyst for a dehydration reaction for producing a dianhydrosugar alcohol from a sugar alcohol.

Advantageous Effects of Invention

As seen from the above description, according to the present invention, as compared with the use of a conventional sulfuric acid catalyst, catalyst separation after the reaction is easy and the load on the reaction apparatus can be decreased in a reaction for obtaining a dianhydrosugar alcohol (for example, isosorbide) from a sugar alcohol (for example, sorbitol). In addition, according to the present invention, a catalyst that can achieve a high selectivity and a high yield, preferably at a lower temperature and in a shorter time, in the above reaction, and that also has excellent regeneration performance during the repeated use of the catalyst, compared with a conventional solid catalyst, is provided. Furthermore, according to the present invention, an improved method for producing a dianhydrosugar alcohol (for example, isosorbide) from a sugar alcohol (for example, sorbitol) by using said catalyst is provided.

BRIEF DESCRIPTION OF DRAWINGS

FIG. 1 shows the chemical reaction formula of a reaction for obtaining isosorbide from sorbitol.

FIG. 2 shows a graph obtained by plotting an isosorbide yield $\eta_1$ and a total yield of by-products $\eta_2$ with respect to a Si/Al ratio regarding zeolites disclosed in Examples and Comparative Examples in Patent Literature 1 based on data in Table 1.

FIG. 3 is a graph showing the relationship between an isosorbide yield and the type of a zeolite and a Si/Al ratio.

DESCRIPTION OF EMBODIMENTS

The present invention relates to a solid catalyst for a dehydration reaction for producing a dianhydrosugar alcohol from a sugar alcohol, comprising an H-type β zeolite in which the atomic composition ratio of Si to Al, Si/Al, is more than 20, and a method for producing a dianhydrosugar alcohol from a sugar alcohol (for example, producing isosorbide from sorbitol) using the same.

As for the sugar alcohol in the present invention, compounds obtained by reducing saccharides, the so-called carbohydrates, to alcohols are used. Said saccharides include saccharides such as aldose and ketose. Examples of sugar alcohols reduced from them and suitable for the present invention include mannitol, iditol and sorbitol. Among them, sorbitol is particularly preferred because the isosorbide that is a produced by its dehydration has a wide variety of uses as a raw material in medicines and plastics.

In the present invention, a dianhydrosugar alcohol refers to a sugar alcohol obtained by removing two molecules of water from a sugar alcohol. For example, when sorbitol is used as a sugar alcohol, various side reactions occur and various intermediates and products can be produced from the sorbitol as described above. In the case of the present invention, preferably, among them, isosorbide is obtained as a dianhydrosugar alcohol. In other words, the above dianhydrosugar alcohol is particularly preferably an isosorbide. Therefore, the present invention will be described below mainly with sorbitol as the sugar alcohol and isosorbide as the dianhydrosugar alcohol, but the description is also similarly applied to other sugar alcohols and the like. For example, when mannitol is used as the above sugar alcohol, preferably, fructose is obtained as the dianhydrosugar alcohol.

In order to achieve the objects of the present invention, it is preferred that the solid catalyst used in the above dehydration reaction in the present invention has a catalyst effect in each of the condensation reactions in two stages in FIG. 1 and can be efficiently separated and removed from the reaction system and moreover does not damage equipment or the environment. From such a viewpoint, in the present invention, β zeolites are adopted, and among them, particularly H-type β zeolites are preferred.

Therefore, the solid catalyst for a dehydration reaction in the present invention is a catalyst containing a β zeolite, preferably a catalyst containing an H-type β zeolite.

The catalyst can comprise, for example, a binder and silica, in addition to the β zeolite, in a range that does not impair the effects of the present invention.

In addition, the catalyst can also comprise the β zeolite as the only component, in other words, the above catalyst can also consist of only the β zeolite. In this case, the present invention relates to a solid catalyst for a dehydration reaction for producing a dianhydrosugar alcohol from a sugar alcohol, which is a β zeolite, preferably an H-type β zeolite.

Here, a zeolite is a generic term for crystalline porous aluminosilicates, and in the present invention, among zeolites, β zeolites (also described as "beta-type zeolites"), preferably H-type β zeolites, are used as described above.

A β zeolite is a synthetic zeolite in which the unit cell composition is represented by the following average composition formula:

$$M_{m/x}[Al_m Si_{(64-m)} O_{128}] \cdot pH_2O$$

wherein M is a cationic species (for example, Na⁺), x is a valence of the above M, m is a number of larger than 0 and less than 64, and p is a number of 0 or more.

In addition, an acid type β zeolite is also referred to as an H-type β zeolite or a proton-type β zeolite and has a structure obtained by ion-exchanging the cationic sites of the β zeolite and replacing them by $H^+$. When the H-type β zeolite is used in the present invention, a slight amount of M that is not replaced may be contained in the H-type β zeolite in a range that does not impair the effects of the present invention. H-type β zeolites are widely used for catalysts for various reactions, adsorbents for chemical substances or the like, because their $H^+$ acts as a Bronsted acid.

Therefore, a method for producing the aforementioned H-type β zeolite is already known, and various products are commercially available. For example, as H-type β zeolites that can be used in the present invention, H-BEA-25 (Si/Al=12.5) manufactured by Clariant Catalysts (Japan) K.K., H-BEA-35 (Si/Al=17.5) manufactured by Clariant Catalysts (Japan) K.K., H-BEA-50 (Si/Al=25) manufactured by Clariant Catalysts (Japan) K.K., H-BEA-150 (Si/Al=75) manufactured by Clariant Catalysts (Japan) K.K., and the like are commercially available.

In the H-type β zeolite in the present invention, the atomic composition ratio of Si to Al, Si/Al ratio, needs to be more than 20 and can also be, for example, 22 or more or 24 or more. When the Si/Al ratio is 20 or less, the yield of isosorbide decreases. It is considered that an H-type β zeolite having a Si/Al ratio of 20 or less generally has a high acidity, and therefore it is expected that the yield is high when the Si/Al ratio is 20 or less, whereas such is not the case, and the yield increases in the case of higher Si/Al ratios. The reasons are not clear. It is presumed that when the Si/Al ratio is 20 or less, the acid content is large, but the acid strength is insufficient. Or the fact that the acid content is too large, and therefore the amount of carbon deposited on the catalyst surface increases, and the reaction is inhibited is also presumed as another factor. Furthermore, the fact that at a Si/Al ratio of 20 or less, factors in terms of shapes such as pore diameter and pore volume decrease isosorbide selectivity is also presumed as one of the reasons.

The atomic composition ratio of Si to Al (Si/Al ratio) can be measured by chemical analysis or elemental analysis by an atomic absorption method.

When the atomic composition ratio of Si to Al (Si/Al ratio) is too large, the acidity of the H-type β zeolite decreases, and the reaction yield decreases; this is not practical. Therefore, in the H-type β zeolite in the present invention, the Si/Al ratio is preferably 400 or less and can be, for example, 300 or less, 200 or less, 100 or less, or 80 or less.

Therefore, the Si/Al ratio of the H-type β zeolite is preferably, for example, in the range of 20<Si/Al ratio≤400, 20<Si/Al ratio≤200, 22≤Si/Al ratio≤100, or 24≤Si/Al ratio≤80.

In addition, the H-type β zeolite in the present invention can have, for example, a specific surface area of 50 m²/g to 1000 m²/g. When the specific surface area is too small, the adsorption performance of the H-type β zeolite is not sufficient. Conversely, when the specific surface area is too large, the following problem is likely to occur: the desorption of the product is prevented and the yield is likely to decrease. From such a viewpoint, the H-type β zeolite in the present invention preferably has a specific surface area of 100 m²/g to 800 m²/g, particularly preferably 400 m²/g to 600 m²/g.

The method for producing a dianhydrosugar alcohol (for example, isosorbide) from a sugar alcohol (for example, sorbitol) using the solid catalyst of the present invention comprises bringing a sugar alcohol (for example, sorbitol) into contact with the catalyst. In this case, for example, the reaction may be carried out by mixing sorbitol in the form of a solid as it is with the catalyst, or the reaction can also be carried out by mixing sorbitol with the catalyst after the former is turned into the form of a liquid, preferably the form of an aqueous solution.

The mixing can be performed, for example, by stirring, and the stirring can be performed using a stirring bar, a stirring blade or similar. In bringing a sugar alcohol (for example, sorbitol) into contact with the catalyst, for example, when the amounts of these are small, they are stirred and mixed using a stirring bar. When the amounts of these increase, stirring can be performed by a motor-driven ribbon type stirring blade or similar.

In one preferred embodiment of the present invention, when a sugar alcohol is brought into contact with the catalyst, mixing is performed using a stirring bar or a stirring blade because uniform and sufficient mixing can be achieved.

In such a dehydration reaction of sorbitol, when the amount of the H-type β zeolite contained in the catalyst (hereinafter also simply referred to as "the amount of the catalyst" for convenience) is too small, a sufficient reaction rate is not obtained, and the conversion of sorbitol decreases. On the other hand, when the amount of the catalyst is too large, not only is the catalyst wasted, but side reactions are promoted, and the yield of isosorbide conversely decreases. From such a viewpoint, in the present invention, the amount of the catalyst is preferably 5 to 60 parts by mass, based on 100 parts by mass of sorbitol. The amount of the catalyst is more preferably 10 to 60 parts by mass, more preferably 20 to 60 parts by mass or 25 to 60 parts by mass, based on 100 parts by mass of sorbitol.

The dehydration reaction of the present invention is accompanied by many side reactions, and therefore the control of the reaction temperature is important. When the reaction temperature is too low, the reaction rate is small and a long reaction time is necessary and therefore the practicality is insufficient. When the temperature is too high, the desired isosorbide selectivity decreases, and the amount of by-products increases. From such a viewpoint, a preferred reaction temperature in the present invention is about 110°

C. to about 170° C., more preferably 115° C. to 160° C., and particularly preferably 120° C. to 150° C., or 120° C. to 145° C., or 125° C. to 135° C.

In addition, the dehydration reaction in the present invention can be performed by maintaining the sugar alcohol brought into contact with the catalyst under any pressure. The dehydration reaction is preferably performed under ambient pressure or under reduced pressure, and more preferably performed under reduced pressure, for example, under a pressure of 1000 hPa or less, 850 hPa or less, 750 hPa or less, 500 hPa or less, 400 hPa or less, or 10 hPa or less. On the other hand, the lower limit of the pressure only depends on the reaction apparatus used and is not particularly limited, and it is generally sufficient that the reaction is carried out under a pressure of 5 hPa to ambient pressure.

The reaction time of the dehydration reaction in the present invention is preferably 1 hour or more, more preferably 1.5 hours or more, because when the reaction time is too short, a sufficient isosorbide yield cannot be achieved. However, when the reaction time is too long, cost increase as well as an increase in the generation of by-products are concerns. From such a viewpoint, the reaction time is preferably 1 hour to 10 hours, more preferably 1.5 hours to 8 hours, and particularly preferably 2 hours to 6 hours.

For example, in the method of the present invention, it is possible to mix the H-type β zeolite that is a solid acid catalyst, as it is, with a sugar alcohol in the solid state of the raw material, and carry out the reaction at a predetermined temperature for a predetermined time as described above, and it is possible to carry out the reaction in a so-called batchwise method. Or it is also possible to fill a reaction tube with a shaped H-type β zeolite catalyst, introduce therein a sugar alcohol turned into the form of a liquid, and continuously react it in a flow.

By extraction with water of the mixture of the products and the remaining raw material (sorbitol) and the catalyst after the reaction, followed by filtration, the catalyst and the products can be separated. The catalyst separated by the filtration can be reused after being dried and calcined.

As described above, in the dehydration reaction of sorbitol, many types of intermediates can be produced, and only particular ones among them can produce isosorbide. With the catalyst of the present invention and the method of the present invention using said catalyst, the intended production of isosorbide with a high selectivity and a high yield is achieved.

The present invention will be described below in Examples, but the present invention is not limited in any way by these Examples and the like.

EXAMPLES

Example 1

182 mg of a sorbitol powder (manufactured by KANTO CHEMICAL CO., INC.) was put in a reaction container (flask) and mixed well with 50 mg of an H-type beta zeolite (H-BEA-50 manufactured by Clariant Catalysts (Japan) K.K., Si/Al=25). The flask containing the mixture of the sorbitol and H-BEA-50 was heated in an oil bath to 130° C. and further maintained at 130° C. for 2 hours (ambient pressure). 20 ml of water was added to the mixture followed by filtration to separate H-BEA-50. The aqueous solution was analyzed by high performance liquid chromatography, and the products were quantified. The yield of isosorbide was 65%.

Example 2

A reaction was performed using the same method and conditions as Example 1 except that H-BEA-150 (manufactured by Clariant Catalysts (Japan) K.K., H-type β zeolite, Si/Al=75) was used instead of H-BEA-50. The reaction was carried out six times in total with the reaction time changed to 0.5 hours, 1 hour, 1.5 hours, 2 hours, 3 hours, and 4 hours. The yield of isosorbide was 17% for 0.5 hours; 40% for 1 hour and 62% for 1.5 hours; and 68% for all of 2 hours, 3 hours, and 4 hours.

Example 3

A reaction was carried out as in Example 2 except that the reaction temperature was 140° C. The yield of isosorbide was 42% for a reaction time of 0.5 hours, 67% in the case of 1 hour, 68% for 1.5 hours, 65% for 2 hours, 62% for 3 hours, and 59% for 4 hours.

Example 4

A reaction was performed using the same method and conditions as Example 1 except that the reaction temperature was 120° C. The reaction was carried out seven times in total with the reaction time changed to 1 hour, 2 hours, 3 hours, 4 hours, 5 hours, 7 hours, and 8 hours. The yield of isosorbide was 14% for a reaction time of 1 hour, 32% when the reaction time was 2 hours, 58% for 3 hours, 68% for 4 hours, 74% for 5 hours, 70% for 7 hours, and 70% for 8 hours.

Example 5

A reaction was performed for 5 hours using the same method as Example 2 using the same unused catalyst (H-BEA-150) as Example 2. The yield of isosorbide at this time was 74%. The catalyst after use was recovered by filtration, dried at 120° C. for 5 hours, and then calcined in air at 500° C. for 3 hours to regenerate the catalyst. Repeating the reaction and regeneration 4 times, the results showed that the first repetition gave 74% of isosorbide yield equivalent to that of the unused catalyst, the yield of isosorbide in the second repetition was 71%, 66% in the third repetition and 62% in the fourth repetition was.

Example 6

A reaction was performed at 140° C. for 2.5 hours using the same method as Example 2 except that 0.26 g (sorbitol content 0.182 g) of a commercial sorbitol aqueous solution (manufactured by KANTO CHEMICAL CO., INC., concentration 70% by mass) was mixed with 0.05 g of an H-BEA-150 catalyst. The yield of isosorbide at this time was 57%.

Comparative Example 1

A reaction was carried out as in Example 1 except that an H-type mordenite zeolite (manufactured by Clariant Catalysts (Japan) K.K., Si/Al=45) was used. The yield of isosorbide was 3%.

Comparative Example 2

A reaction was carried out as in Example 1 except that H-type ZSM-5 (Si/Al=40) was used. The yield of isosorbide was 27%.

Comparative Example 3

A reaction was carried out as in Example 1 except that an H-type Y zeolite (manufactured by Clariant Catalysts (Japan) K.K., HUSY, Si/Al=40) was used. The yield of isosorbide was 22%.

Comparative Example 4

A reaction was carried out as in Example 1 except that H-BEA-35 (manufactured by Clariant Catalysts (Japan) K.K., H-type β zeolite, Si/Al=17.5) was used. The yield of isosorbide was 15%.

Comparative Example 5

A reaction was carried out as in Example 1 except that Nafion-Silica (manufactured by Sigma-Aldrich) that was a cation exchange resin was used. The yield of isosorbide is 66%. Due to the carbon deposition, the catalyst became black and couldn't regenerate for reuse.

Comparative Example 6

A reaction was carried out as in Example 1 except that a sulfuric acid that was a homogeneous catalyst was used. The yield of isosorbide was 61%.

The experimental results of Examples 1 to 4, Example 6, and Comparative Examples 1 to 6 are shown together in Table 2. In addition, the experimental results of Example 5 are shown in Table 3.

As can be seen from Table 2, with the catalyst of the present invention (H-BEA-150), a conversion efficiency of almost 100% and a high selectivity of 67% were obtained in the reaction at 140° C. for 1 hour. In the reaction at 120° C., lower than 140° C., a high isosorbide selectivity value of 74% was obtained in 5 hours.

In addition, Table 3 shows that under the reaction conditions of 120° C. and 5 hours, a practical high yield of 60% or more is obtained. The catalyst can be reused at least four times after regeneration.

TABLE 2

Experimental Results of Examples 1 to 4, Example 6, and Comparative Examples 1 to 6

| | Time (hr) | Catalyst Name | Si/Al | Yield (%) Isosorbide | 1,4-Sorbitan | 2,5-Mannitan | Others | Sorbitol |
|---|---|---|---|---|---|---|---|---|
| Example 1 (130° C.) | 2 | H-BEA-50 | 25 | 65 | 6 | 3 | 26 | 0 |
| Example 2 (130° C.) | 0.5 | H-BEA-150 | 75 | 17 | 36 | 1 | 11 | 35 |
| | 1 | H-BEA-150 | 75 | 40 | 27 | 2 | 19 | 12 |
| | 1.5 | H-BEA-150 | 75 | 62 | 12 | 2 | 22 | 2 |
| | 2 | H-BEA-150 | 75 | 68 | 5 | 2 | 24 | 1 |
| | 3 | H-BEA-150 | 75 | 68 | 2 | 2 | 28 | 0 |
| | 4 | H-BEA-150 | 75 | 68 | 1 | 2 | 29 | 0 |
| Example 3 (140° C.) | 0.5 | H-BEA-150 | 75 | 42 | 24 | 2 | 21 | 11 |
| | 1 | H-BEA-150 | 75 | 67 | 6 | 3 | 23 | 1 |
| | 1.5 | H-BEA-150 | 75 | 68 | 2 | 3 | 27 | 0 |
| | 2 | H-BEA-150 | 75 | 65 | 1 | 3 | 31 | 0 |
| | 3 | H-BEA-150 | 75 | 62 | 1 | 2 | 35 | 0 |
| | 4 | H-BEA-150 | 75 | 59 | 1 | 2 | 38 | 0 |
| Example 4 (120° C.) | 1 | H-BEA-150 | 75 | 14 | 36 | 1 | 9 | 40 |
| | 2 | H-BEA-150 | 75 | 32 | 32 | 2 | 19 | 15 |
| | 3 | H-BEA-150 | 75 | 58 | 16 | 2 | 22 | 2 |
| | 4 | H-BEA-150 | 75 | 68 | 7 | 2 | 22 | 1 |
| | 5 | H-BEA-150 | 75 | 74 | 1 | 2 | 23 | 0 |
| | 7 | H-BEA-150 | 75 | 70 | 1 | 2 | 27 | 0 |
| | 8 | H-BEA-150 | 75 | 70 | 1 | 2 | 27 | 0 |
| Example 6 (140° C.) | 2.5 | H-BEA-150 | 75 | 57 | 19 | 3 | 19 | 2 |
| Comparative Example 1 | 2 | HMOR | 45 | 3 | 12 | 1 | 8 | 76 |
| Comparative Example 2 | 2 | HZSM-5 | 40 | 27 | 9 | 1 | 17 | 46 |
| Comparative Example 3 | 2 | HUSY | 40 | 22 | 30 | 9 | 29 | 10 |
| Comparative Example 4 | 2 | H-BEA-35 | 17.5 | 15 | 23 | 1 | 5 | 52 |
| Comparative Example 5 | 2 | Nafion | | 66 | 9 | 4 | 23 | 0 |
| Comparative Example 6 | 2 | $H_2SO_4$ | | 61 | 13 | 4 | 22 | 0 |

TABLE 3

Experimental Results of Example 5

| | Number of reactions | Catalyst Name | Si/Al | Yield (%) | | | | |
|---|---|---|---|---|---|---|---|---|
| | | | | Isosorbide | 1,4-Sorbitan | 2,5-Mannitan | Others | Sorbitol |
| Example 5 (120° C., 5 hours) recovery, repeated use | First repetition | H-BEA-150 | 75 | 74 | 1 | 2 | 23 | 0 |
| | Second repetition | H-BEA-150 | 75 | 71 | 1 | 2 | 26 | 0 |
| | Third repetition | H-BEA-150 | 75 | 66 | 6 | 2 | 26 | 0 |
| | Fourth repetition | H-BEA-150 | 75 | 62 | 10 | 2 | 25 | 1 |

Example 7

A reaction was carried out as in Example 2 except that the pressure was reduced to 700 hPa, and stirring was performed by a stirring bar. The isosorbide yield after 4 hours of reaction was 74%, an increase compared with 68% in Example 2.

Example 8

A reaction was carried out as in Example 3 except that the pressure was reduced to 700 hPa, and stirring was performed by a stirring bar. The isosorbide yield after 1 hour of reaction was 70%, an increase compared with 67% in Example 3.

Example 9

A reaction was carried out as in Example 4 except that the pressure was reduced to 700 hPa, and stirring was performed by a stirring bar. The isosorbide yield after 7 hours of reaction was 73%, an increase compared with 70% in Example 4.

The experimental results of Examples 7 to 9 are shown in Table 4. By reducing pressure and stirring, the yield of isosorbide can be increased. Therefore, the dehydration reaction of sorbitol was tested again under this reduced pressure condition by varying not only the catalysts but also the amounts.

Example 10

A reaction was carried out as in Example 7 except that the amount of the catalyst used was 12.5 mg. The yield of isosorbide after 2 hour of reaction was 23%.

Example 11

A reaction was carried out as in Example 7 except that the amount of the catalyst used was 25 mg. The yield of isosorbide after 3 hour of reaction was 51%.

Example 12

A reaction was carried out as in Example 7 except that the amount of the catalyst used was 37.5 mg. The yield of isosorbide after 2 hours of reaction was 62%.

Example 13

A reaction was carried out as in Example 7 except that the amount of the catalyst used was 75 mg. The yield of isosorbide after 2 hours of reaction was 72%.

Example 14

A reaction was carried out as in Example 7 except that the amount of the catalyst used was 100 mg. The yield of isosorbide after 2 hours of reaction was 70%.

TABLE 4

Experimental Results of Examples 7 to 9

| | Reaction time (h) | Catalyst Name | Si/Al | Yield (%) | | | | |
|---|---|---|---|---|---|---|---|---|
| | | | | Isosorbide | 1,4-Sorbitan | 2,5-Mannitan | Others | Sorbitol |
| Example 7 (130° C.) | 0.25 | H-BEA-150 | 75 | 7 | 31 | 1 | 9 | 53 |
| | 0.5 | H-BEA-150 | 75 | 24 | 39 | 2 | 13 | 25 |
| | 1 | H-BEA-150 | 75 | 50 | 25 | 1 | 21 | 5 |
| | 2 | H-BEA-150 | 75 | 71 | 5 | 3 | 23 | 1 |
| | 4 | H-BEA-150 | 75 | 74 | 2 | 2 | 24 | 1 |
| | 6 | H-BEA-150 | 75 | 74 | 2 | 2 | 24 | 0 |
| Example 8 (140° C.) | 0.5 | H-BEA-150 | 75 | 56 | 18 | 3 | 23 | 3 |
| | 1 | H-BEA-150 | 75 | 70 | 2 | 3 | 25 | 0 |
| | 2 | H-BEA-150 | 75 | 72 | 2 | 3 | 26 | 0 |
| | 4 | H-BEA-150 | 75 | 73 | 1 | 2 | 26 | 1 |
| Example 9 (120° C.) | 1 | H-BEA-150 | 75 | 22 | 38 | 1 | 14 | 26 |
| | 2 | H-BEA-150 | 75 | 46 | 28 | 1 | 22 | 4 |
| | 5 | H-BEA-150 | 75 | 71 | 3 | 2 | 25 | 2 |
| | 7 | H-BEA-150 | 75 | 73 | 3 | 3 | 25 | 0 |

Example 15

A reaction was carried out as in Example 7 except that the pressure was <10 hPa. The yield of isosorbide after 2 hours of reaction was 75%.

Example 16

A reaction was carried out as in Example 7 except that the pressure was 350 hPa. The yield of isosorbide after 2 hours of reaction was 72%.

Example 17

A reaction was carried out as in Example 7 except that the pressure was 1000 hPa. The yield of isosorbide after 2 hours of reaction was 71%.

Example 18

A reaction was carried out as in Example 7 except that H-BEA-50 (H-type β zeolite, Si/Al=25) calcined at 550° C. for 8 hours was used. The yield of isosorbide after 2 hours of reaction was 68%.

Comparative Example 7

A reaction was carried out as in Example 7 except that H-BEA-25 (manufactured by Clariant Catalysts (Japan) K.K., H-type β zeolite, Si/Al=12.5) calcined at 550° C. for 8 hours was used. The yield of isosorbide after 2 hours of reaction was 41%.

Comparative Example 8

A reaction was carried out as in Example 7 except that H-BEA-35 (H-type β zeolite, Si/Al=17.5) calcined at 550° C. for 8 hours was used. The yield of isosorbide after 2 hours of reaction was 51%.

Comparative Example 9

A reaction was carried out as in Example 7 except that an H-type ZSM-5 zeolite (Si/Al=12.5) was used. The yield of isosorbide after 2 hours of reaction was 9%.

Comparative Example 10

A reaction was carried out as in Example 7 except that an H-type ZSM-5 zeolite (Si/Al=45) was used. The yield of isosorbide after 2 hours of reaction was 27%.

Comparative Example 11

A reaction was carried out as in Example 7 except that an H-type Y zeolite (Si/Al=2.6) was used. The yield of isosorbide after 2 hours of reaction was 0%.

Comparative Example 12

A reaction was carried out as in Example 7 except that an H-type Y zeolite (Si/Al=15) was used. The yield of isosorbide after 2 hours of reaction was 2%.

Comparative Example 13

A reaction was carried out as in Example 7 except that an H-type Y zeolite (Si/Al=40) was used. The yield of isosorbide after 2 hours of reaction was 22%.

Comparative Example 14

A reaction was carried out as in Example 7 except that an H-type mordenite (Si/Al=45) was used. The yield of isosorbide after 2 hours of reaction was 3%.

Comparative Example 15

A reaction was carried out as in Example 7 except that a sulfuric acid was used. The yield of isosorbide after 2 hours of reaction was 69%.

The experimental results of Examples 10 to 18 and Comparative Examples 7 to 15 are shown in Table 5. In addition, results obtained by plotting the isosorbide yield after 2 hour of the reaction in Examples 7 and 18 and Comparative Examples 7 to 14 with respect to the Si/Al ratio are shown in FIG. 3. It is seen that the H-type β zeolites having an Si/Al ratio of more than 20 specifically provide isosorbide with a high yield.

TABLE 5

Experimental Results of Examples 10 to 18 and Comparative Examples 7 to 15

| | Reaction time (h) | Pressure (hPa) | Catalyst Name | Si/Al | Amount of catalyst (mg) | Yield (%) Isosorbide | 1,4-Sorbitan | 2,5-Mannitan | Others | Sorbitol |
|---|---|---|---|---|---|---|---|---|---|---|
| Example 10 | 2 | 700 | H-BEA-150 | 75 | 12.5 | 23 | 36 | 2 | 11 | 29 |
| Example 11 | 2 | 700 | H-BEA-150 | 75 | 25 | 51 | 27 | 3 | 15 | 4 |
| Example 12 | 2 | 700 | H-BEA-150 | 75 | 37.5 | 62. | 15 | 3 | 18 | 2 |
| Example 13 | 2 | 700 | H-BEA-150 | 75 | 75 | 72 | 2 | 3 | 24 | 0 |
| Example 14 | 2 | 700 | H-BEA-150 | 75 | 100 | 70 | 2 | 2 | 26 | 0 |
| Example 15 | 2 | <10 | H-BEA-150 | 75 | 50 | 75 | 2 | 3 | 19 | 2 |
| Example 16 | 2 | 350 | H-BEA-150 | 75 | 50 | 72 | 2 | 3 | 23 | 0 |
| Example 17 | 2 | 1000 | H-BEA-150 | 75 | 50 | 71 | 3 | 3 | 22 | 1 |
| Example 18 | 2 | 700 | H-BEA-50 | 25 | 50 | 68 | 6 | 3 | 20 | 3 |
| Comparative Example 7 | 2 | 700 | H-BEA-25 | 12.5 | 50 | 41 | 30 | 3 | 16 | 11 |
| Comparative Example 8 | 2 | 700 | H-BEA-35 | 17.5 | 50 | 51 | 21 | 3 | 18 | 7 |
| Comparative Example 9 | 2 | 700 | HZSM-5 | 12.5 | 50 | 9 | 6 | 0 | 13 | 73 |

TABLE 5-continued

Experimental Results of Examples 10 to 18 and Comparative Examples 7 to 15

| | Reaction time (h) | Pressure (hPa) | Catalyst Name | Catalyst Si/Al | Amount of catalyst (mg) | Yield (%) Isosorbide | 1,4-Sorbitan | 2,5-Mannitan | Others | Sorbitol |
|---|---|---|---|---|---|---|---|---|---|---|
| Comparative Example 10 | 2 | 700 | HZSM-5 | 45 | 50 | 27 | 7 | 1 | 15 | 50 |
| Comparative Example 11 | 2 | 700 | HY | 2.6 | 50 | 0 | 0 | 0 | 0 | 100 |
| Comparative Example 12 | 2 | 700 | HY | 15 | 50 | 2 | 9 | 2 | 15 | 7 |
| Comparative Example 13 | 2 | 700 | HY | 40 | 50 | 22 | 20 | 7 | 43 | 8 |
| Comparative Example 14 | 2 | 700 | HMOR | 45 | 50 | 3 | 14 | 1 | 7 | 77 |
| Comparative Example 15 | 2 | 700 | $H_2SO_4$ | | 1.1 | 69 | 3 | 4 | 24 | 1 |

The invention claimed is:

1. A solid, catalyst for a dehydration catalyst, comprising an H-type β zeolite having an atomic composition ratio of Si to Al (Si/Al) of more than 20.

2. The solid, dehydration catalyst according to claim 1, wherein the Si/Al ratio is 400 or less.

3. A method for producing a dianhydrosugar alcohol from a sugar alcohol, comprising bringing the sugar alcohol into contact with the catalyst according to claim 1.

4. The method according to claim 3, wherein the amount of the H-type β zeolite contained in the catalyst is 5 to 60 parts by mass, based on 100 parts by mass of the sugar alcohol.

5. The method according to claim 3, further comprising maintaining the sugar alcohol brought into contact with the catalyst under ambient pressure or under reduced pressure.

6. The method according to claim 3, further comprising maintaining the sugar alcohol brought into contact with the catalyst at a temperature of 110° C. to 170° C.

7. The method according to claim 3, further comprising maintaining the sugar alcohol brought into contact with the catalyst for 1.5 hours or more.

8. The method according to claim 3, wherein the sugar alcohol is selected from the group consisting of sorbitol, mannitol and iditol.

9. The method according to claim 3, wherein the sugar alcohol is sorbitol, and the dianhydrosugar alcohol is isosorbide.

\* \* \* \* \*

UNITED STATES PATENT AND TRADEMARK OFFICE
CERTIFICATE OF CORRECTION

PATENT NO. : 9,920,064 B2
APPLICATION NO. : 15/322584
DATED : March 20, 2018
INVENTOR(S) : Atsushi Fukuoka et al.

It is certified that error appears in the above-identified patent and that said Letters Patent is hereby corrected as shown below:

Column 17, Line 24, cancel the text "catalyst for a."

Signed and Sealed this
Fifteenth Day of May, 2018

Andrei Iancu
*Director of the United States Patent and Trademark Office*